(12) United States Patent
Yung (10) Patent No.: US 7,439,223 B2
(45) Date of Patent: Oct. 21, 2008

(54) NUCLEOPHOSMIN/B23-BINDING PEPTIDE TO INHIBIT TUMOR GROWTH AND REGULATE TRANSCRIPTIONAL ACTIVITY OF P53

(75) Inventor: Benjamin Yat Ming Yung, Tao-Yuan (TW)

(73) Assignee: Chang Gung University, Tao-Yuan (TW)

( * ) Notice: Subject to any disclaimer, the term of this patent is extended or adjusted under 35 U.S.C. 154(b) by 376 days.

(21) Appl. No.: 11/239,032

(22) Filed: Sep. 30, 2005

(65) Prior Publication Data

US 2007/0254845 A1     Nov. 1, 2007

(51) Int. Cl.
*A61K 38/00* (2006.01)
(52) U.S. Cl. .......................................... 514/2; 435/375
(58) Field of Classification Search ....................... None
See application file for complete search history.

(56) References Cited

OTHER PUBLICATIONS

Korgaonkar et al. (Molecular and Cellular Biology, vol. 25, No. 4, pp. 1258-1271, Feb. 2005).*
Janssen et al. (International Journal of Pharmaceutics, vol. 254, pp. 55-58, 2003).*
Hui Jia Chan, et al., Nucleophosmin/B23-binding Peptide Inhibits Tumor Growth and Up-Regulates Transcriptional Activity of p53; Science Direct, Apr. 25, 2005.

* cited by examiner

*Primary Examiner*—Larry R. Helms
*Assistant Examiner*—Meera Natarajan
(74) *Attorney, Agent, or Firm*—Rosenberg, Klein & Lee (57) ABSTRACT

The Rev peptide that binds to nucleophosmin/B23 with the highest affinity exhibits the greatest cytotoxicity on Ras-3T3 cells and inhibits tumor growth most effectively in nude mice. The efficiency of colony formation in soft agar of Ras-3T3 cells is significantly inhibited by treatment with Rev peptide. In addition, Rev peptide can potentiate the doxorubicin-induced decrease of cellular viability in U1 bladder cancer cells and inhibition of tumor growth in nude mice. Treatment of Rev peptide increases protein expression and transcriptional activity of p53 and inhibits the nucleophosmin/B23-mediated PCNA promoter activation. Peptides having high affinity of binding to molecular targets such as nucleophosmin/B23 represent a useful approach to anti-cancer biotherapeutics.

15 Claims, 10 Drawing Sheets

| Peptide | Sequence | $K_D(\mu M)^a$ |
|---|---|---|
| Rev | ARRNRRRRWREYC | 0.082±0.002 |
| T-NLS | PKKKRKVEDPYC | 0.824±0.016 |
| np-NLS | KRPAATKKAGQAKKKKYC | —$^b$ |

$^a$The dissociation constants were calculated by Szebeni et al., 1995.

$^b$np-NLS shows no detectable binding activity with B23.

Figure 4

NUCLEOPHOSMIN/B23-BINDING PEPTIDE TO INHIBIT TUMOR GROWTH AND REGULATE TRANSCRIPTIONAL ACTIVITY OF P53

BACKGROUND OF THE INVENTION

1. Field of the Invention

The present invention relates to tumors. More specifically, the present invention discloses a method of inhibiting tumor growth and up-regulating transcriptional activity of p53 by utilizing Nucleophosmin/B23-binding peptide.

2. Description of the Prior Art

One important feature that distinguishes between cancerous and normal cells is hyperactivity and pleomorphism of the nucleoli. Although rRNA transcription, processing and ribosome assembly have been established as major functions of nucleolus, previous studies suggest that nucleolus participates in many other aspects of gene expression as well.

New results indicate that biosyntheses of signal recognition particle RNA and telomerase RNA involve a nucleolar stage and that nucleolus is a site critical to cellular aging. A number of studies suggest that nucleophosmin/B23, one of the major nucleolar phosphoproteins, plays a role in increased nucleolar activity that is necessary for cell proliferation. Down-regulation of nucleophosmin/B23 is associated with two different growth control pathways, cellular differentiation and apoptosis. The steady-state level of nucleophosmin/B23 mRNA is significantly higher in abnormal growth than in normal growth.

However, the underlying molecular mechanism is still largely undefined.

SUMMARY OF THE INVENTION

To achieve these and other advantages and in order to overcome the disadvantages of the conventional method in accordance with the purpose of the invention as embodied and broadly described herein, the present invention provides a method of inhibiting tumor growth and up-regulating transcriptional activity of p53.

The sizes of tumor extension and the stages of cancer are related to nucleophosmin/B23 mRNA levels. Cancers of later stages have relatively higher nucleophosmin/B23 mRNA levels than the matched adjacent "normal" tissues. Nucleophosmin/B23 may play a downstream role in the apoptotic cascade as its synthesis decreases during apoptosis in Jurkat T-lymphoblasts. Blockage of nucleophomin/B23 expression with its antisense oligonucleotides has shown that nucleophosmin/B23 is crucial for rendering cancer cells resistant to induction of differentiation and apoptosis.

Therefore an excess of nucleophosmin/B23 is an important cause of cancer and not just a consequence. The potentiation ability of nucleophosmin/B23 antisense in induced cellular differentiation, apoptosis and inhibition of telomerase activity is particularly interesting and could lead to the use of antisense construct in cancer treatment. In any case, nucleophosmin/B23 gene is functionally implicated in growth control, and its expression has a causal relationship with susceptibility of tumor cells to induced differentiation and apoptosis.

The import of proteins into the nucleus via the nuclear pore complex is directed by relatively short basic sequences called nuclear localization signals (NLSs) contained in these proteins. Although the NLS sequences have been identified in a large number of proteins, only a few of the protein receptors to which they bind have been identified. One of these is nucleophosmin/B23, which has been shown to bind peptides containing NLS of the SV40 T-antigen. Furthermore, nucleophosmin/B23 has also been shown to form a specific complex with the human immunodeficiency virus-1 (HIV-1) Rev protein.

A study of determining the relative affinities and stoichiometries of various NLS-containing peptides for nucleophosmin/B23, shows that a peptide (Rev37-47) containing the sequence required for nucleolar localization of the HIV-1 Rev protein has an affinity for nucleophosmin/B23 ten folds greater than that of the SV40 T-NLS. Small molecule that binds to the target of cancer would be a specific and powerful anti-cancer therapeutic agent.

The present invention provides a method of inhibiting tumor growth utilizing nucleophosmin/B23 as the important molecular target for cancer suppression. The peptide, exhibiting high binding affinity toward nucleophosmin/B23 is able to inhibit tumor growth. The anti-tumor effect of the nucleophosmin/B23-binding peptide can be the consequence of increased protein expression of tumor suppressor p53 and its activity. Nucleophosmin/B23 can be associated with p53-mediated signaling pathways that suppress tumor development and growth. Peptides having high affinity of binding to molecular targets such as nucleophosmin/B23 represent a useful approach to anti-cancer biotherapeutics.

These and other objectives of the present invention will become obvious to those of ordinary skill in the art after reading the following detailed description of preferred embodiments.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Reference will now be made in detail to the preferred embodiments of the present invention, examples of which are illustrated in the accompanying drawings. Wherever possible, the same reference numbers are used in the drawings and the description to refer to the same or like parts.

To better illustrate the method of the present invention, the following study is given as example.

Regarding the cells and antibodies, MGH-U1 was established from a Grade III bladder transitional cell carcinoma. U1 and Ras-3T3 cells were grown in RPMI 1640 medium supplemented with 10% fetal bovine serum and 1% antibiotics in 5% CO2 humidified incubator at 37° C. The number of viable cells was determined by trypan blue exclusion and counted with a hemocytometer. Antinucleophosmin/B23 mAb, Anti-p53 polyclonal antibody (pAb) and anti-GAPDH were provided.

Regarding the clonogenic survival, cells were cultured in 6-well plates (Nunc). Cell suspensions in RPMI containing 0.35% agar and 10% fetal calf serum were layered over the 0.5% base layer to a final cell density of $2 \times 10^3$ cells per well. Cells were treated with Rev peptide at 12 hours after seeding. Twelve days posttreatment, clones were stained with 0.5% crystal violet (in 70% methanol) for visualization, and the clones whose diameter was greater than 1 mm were counted. The survival percentage was expressed as the relative seeding efficiency of Rev-treated versus control untreated cultures.

For peptide synthesis, Rev peptide (ARRNRRRWREYC) (SEQ ID NO: 1), T-NLS peptide (PKKKRKVEDPYC) (SEQ ID NO: 2), and np-NLS peptide (KRPAATKKAGQAKKKKYC) (SEQ ID NO: 3) were synthesized manually on solid phase using the Fmoc strategy. This strategy is based on sequential addition of .alpha.-amino and side-chain protected amino acid residues to an insoluble polymeric support Fmoc amino acids were stepwise coupled to Rink Amide MBHA resin by using 2-(1H-Benzotriazole-1-yl)-1,1,3,3-tetramethyluronium hexafluorophosphate as the coupling reagent. The completion of the coupling reactions was qualified by Kaiser test. After the synthesis was finished, 92.5% trifluoroacetic acid (TEA) was used to cleave the peptide from the resin. Most of the TFA was evaporated and the peptide was precipitated in cold ether. Peptides were analyzed by reverse-phase high-performance liquid chromatography (HPLC) on a Walters EPLC system. The following condition was used: column, Beckman Ultrasphere ODS C-18(5. mu.m, 0.46, times.0.25 cm); eluent A, 0.1% (v/v) TFA in $H_2O$; eluent B, acetonitrile; gradient B, 0% over 2 min, 0-80% over 20 min, 80%-0 over 4 min; flow rate, 1 ml/min; absorbance, 216 nm. Only peptides that showed a single peak were used for in vitro and in vivo study. Peptides were lyophilized and stored in –80.degree. C. Prior to use, peptides were dissolved in sterilized PBS.

Exponentially growing Ras-3T3 cells were harvested, washed and resuspended in PBS at $3 \times 10^6$ cells/ml. Tumor xenografts were established by inoculating one hundred microliters (100 μl) of the cell suspension subcutaneously into the right flanks of the nude mice. To assay the antitumor activity of Rev, T-NLS, and np-NLS peptides, they were administered to tumors as a systemic intraperitoneal or as a local subcutaneous treatment. For intraperitoneal treatment, mice were randomized into 4 groups of 5 animals after grafting. Group 1 (controls): daily intraperitoneal injection of PBS (0.2 ml/20 g body weight); group 2: daily intraperitoneal injection of Rev peptide (1.5 mg/20 g body weight); group 3: daily intraperitoneal injection of T6 NLS peptide (10 mg/20 g body weight); group 4: daily intraperitoneal injection of np-NLS peptide (10 mg/20 g body weight).

Animals were treated once daily for 14 days beginning 48 hr after the inoculation of Ras-3T3 cells. For local administration, Rev peptide (1 mg/20 g body weight) was injected subcutaneously adjacent to the tumor once daily for 5 days. Treatment was started about 9 days after xenografting, that was, at a time when the tumor volume had reached a mean volume of $90 \pm 20$ mm$^3$. Three-dimensional measurements were taken with electric caliper and the tumor volumes were calculated using the formula, $V = 4\pi xyz/3$, where 2x, 2y and 2z were the three perpendicular diameters of the tumor. Each experiment was performed three times. Statistical differences in the tumor volumes were analyzed by the student's t-test. During the treatment course, mice were weighted weekly.

pp53-TA-Luc contains a p53 response element, located upstream of the minimal TA promoter, the TATA box from the herpes simplex virus thymidine kinase promoter ($P_{TA}$). Located downstream of $P_{TA}$ is the firefly luciferase reporter gene. Double stranded siRNA oligonucleotides against B23, siB23-297 (sense: 5'-CACCACCAGTGGTCTTAAG; and antisense: CTTAAGACCACTGGTGGTG), and siB23-191 (sense 5'-GCAGAGGCAATGAATTACG and antisense: CGTAATTCATTGCCTCTGC) were synthesized. Two oligonucleotides were annealed and cloned into pSilencer™ siRNA expression vector by EcoR1 and Apa1.

Transfections were performed using Lipofectamine™ Reagent method. Before transfection, cells ($2 \times 10^5$ per well) were seeded in 6-well plates overnight. SiRNA or plasmid DNA (2.5 mg) and Lipofectamine™ Reagent (12.5 mg), each diluted in serum-free medium (150 ml). DNA and Lipofectamine™ Reagent were then mixed and incubated for 30 min at room temperature to allow DNA-liposome complexes formation. Cells were rinsed twice with PBS, and replaced to serum-free medium (0.7 ml), and then overlaid with DNA-liposome complexes. After 6 hours of incubation at 37° C. in $CO_2$ incubator, the DNA-containing medium was replaced by fresh medium containing 10% serum.

Figure 1A:
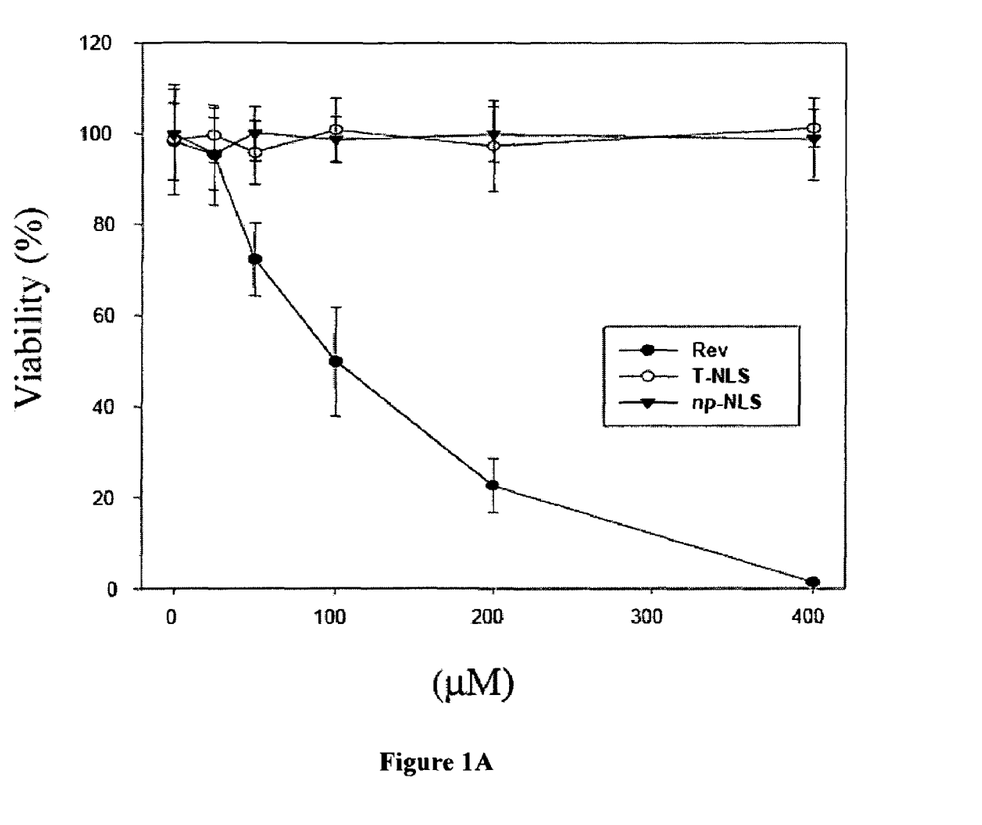
FIGS. 1A-1D are graphs illustrating Nucleophosmin/B23-binding peptide inhibiting tumor growth of Ras-3T3 cells and tumors in nude mice according to embodiments of the present invention.
Figure 4:
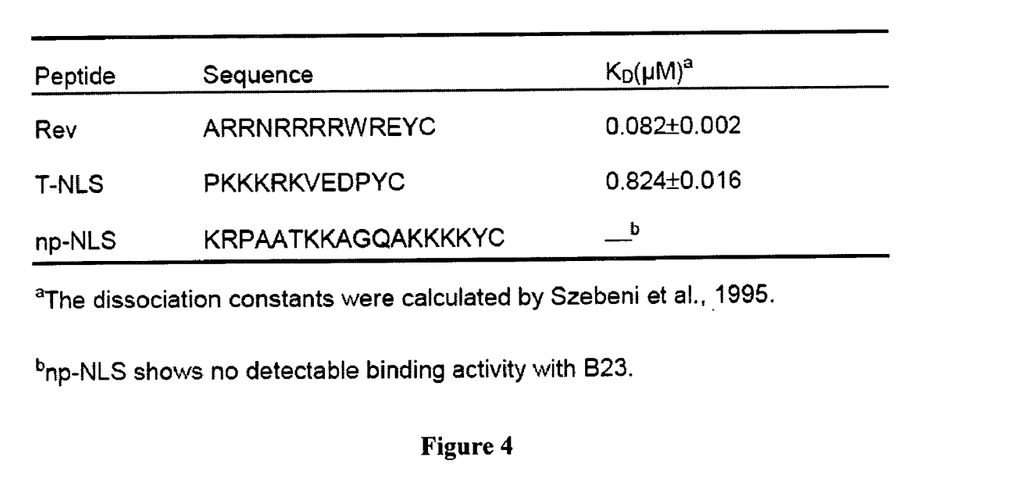
FIG. 4 is a table illustrating the primary sequences of Rev-NLS (Rev), T-NLS and np-NLS peptides and the dissociation constants of their interactions with nucleophosmin/B23.

Rev-NLS (Rev), T-NLS and np-NLS peptides were synthesized. The primary sequences of the peptides and the dissociation constants of their interactions with nucleophosmin/B23 are shown in FIG. 4. Rev, T-NLS, and np-NLS peptides were applied to Ras-3T3 cells in parallel experiments at concentrations ranging from 25 to 400 μM. As shown in FIG. 1A, the Rev peptide that binds to nucleophosmin/B23 with the highest affinity ($k_d = 0.082$ μM) exhibited the greatest cytotoxicity on Ras-3T3 cells. The concentration of Rev peptide at which there was a 50% decrease in cell viability was about 95.1 μM. On the other hand, peptide that shows less binding affinity (T-NLS, $k_d = 0.824$ μM) or no binding affinity (np-NLS) toward nucleophosmin/B23, had little or virtually no effect on cellular viability at the indicated concentrations. The concentration of T-NLS peptide at which there was a 50% decrease in cell viability was about 1 mM. np-NLS showed no activity against cells at 1 mM (data not shown).

Figure 1B:
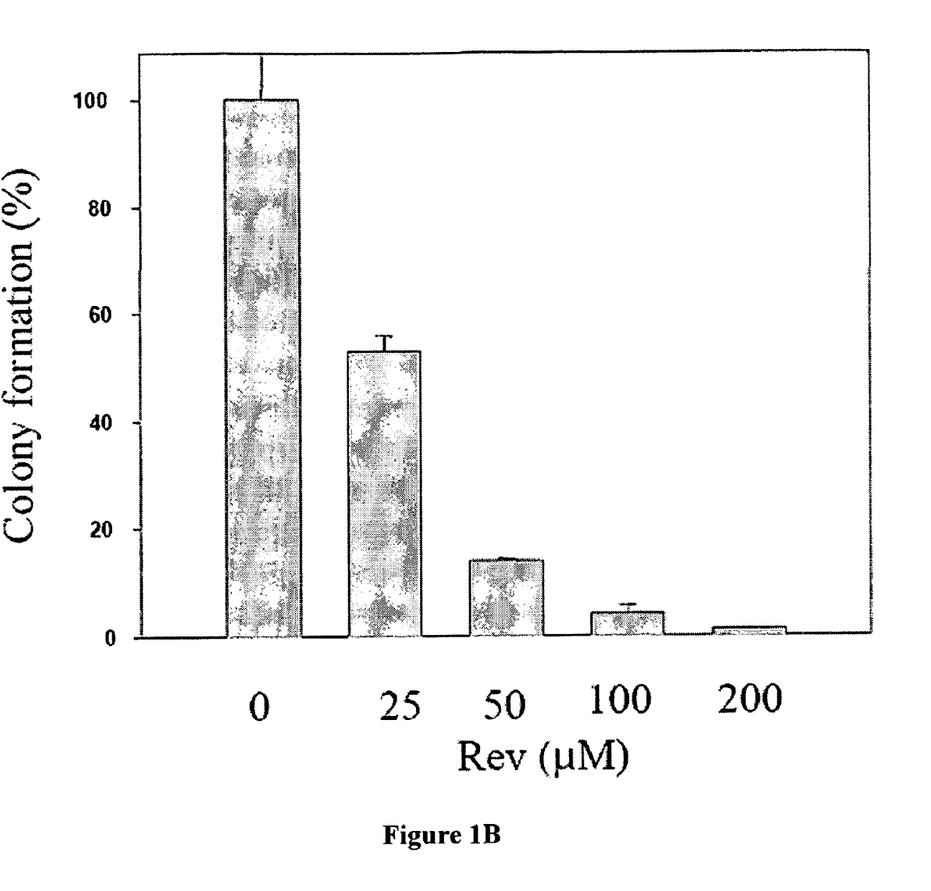

Anchorage-independent growth in soft agar is one important feature of transformed cells. Interestingly, the efficiency of colony formation in soft agar of Ras-3T3 cells was significantly inhibited by treatment with Rev peptide (25-200 μM) (FIG. 1B). Rev peptide could thus reverse the transformed phenotype of Ras-3T3 cells to normal-like phenotype.

Figure 1C:
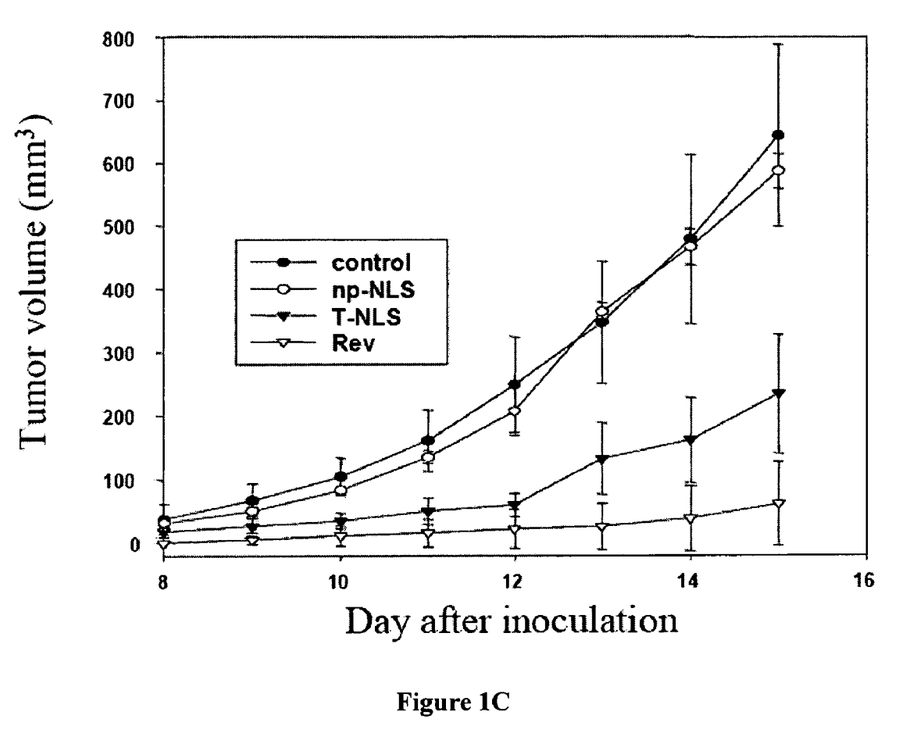

Next, a nude mouse xenograft assay was used to evaluate the antitumor effect of peptides on the growth of tumors induced by Ras-3T3 cells. Ras-3T3 cells were inoculated subcutaneously into the right flanks of nude mice. For intraperitoneal treatment, the mice were randomly assigned to the control (PBS treatment), Rev, T-NLS and np-NLS peptide treatment groups two days after inoculation. During the course of treatment, tumor growth was monitored daily by caliper measurement. As shown in FIG. 1C, the tumor volumes of mice treated with Rev and T-NLS peptides increased with much less extent as compared with those treated with PBS or np-NLS. The Rev peptide (1.5 mg/20 g body weight), which binds nucleophosmin/B23 with the highest affinity, inhibited tumor growth most effectively by 89.1% ($p < 0.05$).

Tumor growth in mice treated with higher dose (10 mg/20 g body weight) of TNLS, which binds nucleophosmin/B23 with lower affinity, was inhibited by 63.6% ($p<0.05$). No inhibition of tumor growth was observed in np-NLStreated (10 mg/20 g body weight) nude mice.

Figure 1D:
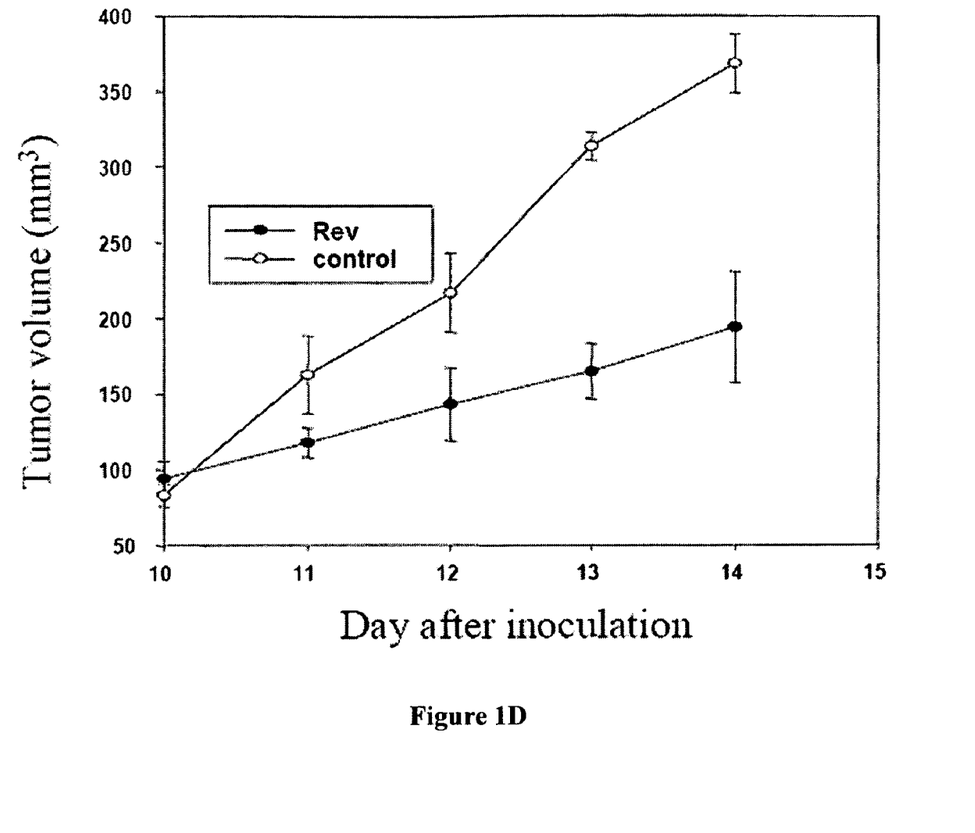

For local treatment, Rev peptide (1 mg/20 g body weight) was administered subcutaneously adjacent to the tumors daily for 5 days. The tumor grew more slowly in mice treated with Rev peptide than the control mice treated with PBS ($p<0.05$) (FIG. 1D). The tumors treated with PBS progressed more quickly, reaching up to about 4.4 times the initial volume while tumors treated with Rev peptide only reached up to about 2.1 times. Virtually there were no changes in body weight in peptide-treated mice as compared to control groups (data not shown). Taken together, these results showed that Rev peptide, when applied locally or intraperitoneally, possessed the greatest inhibitory effect on tumor growth.

Figure 2A:
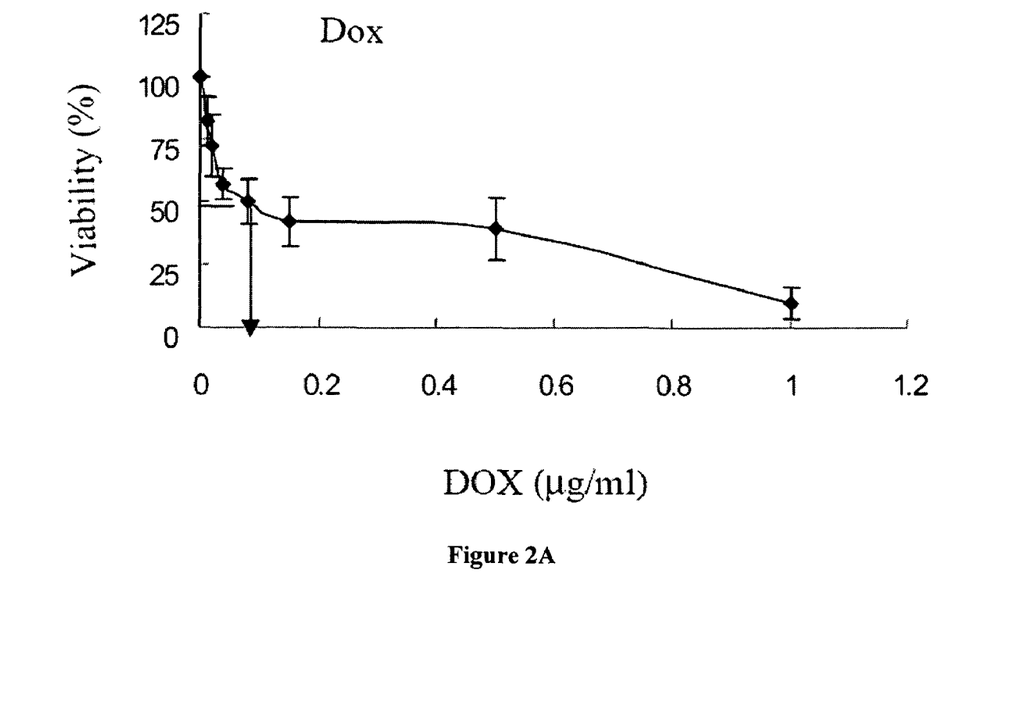
FIGS. 2A-2D are graphs illustrating Rev peptide potentiating doxorubicin-induced anti-tumor activity against U1 bladder cancer cells and tumors in nude mice according to embodiments of the present invention.
Figure 2B:
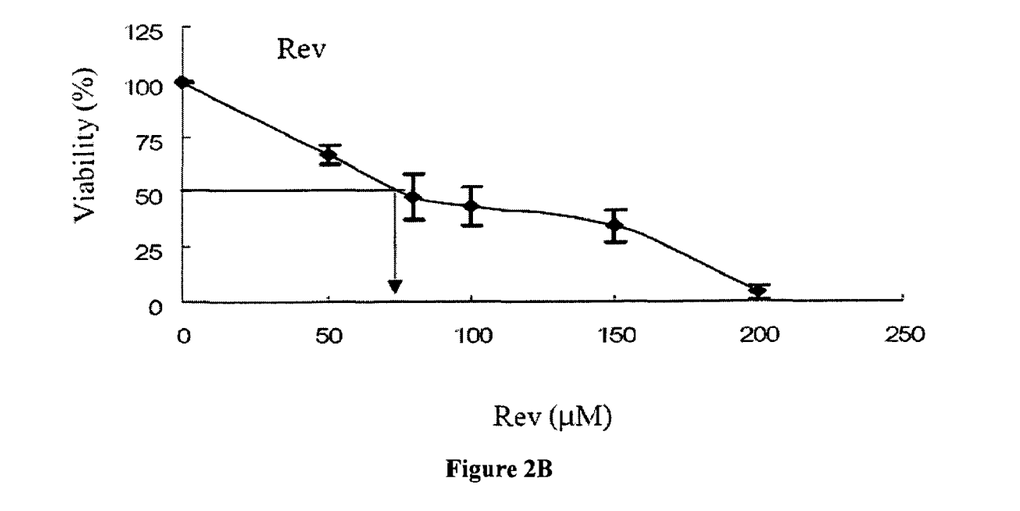
Figure 2C:
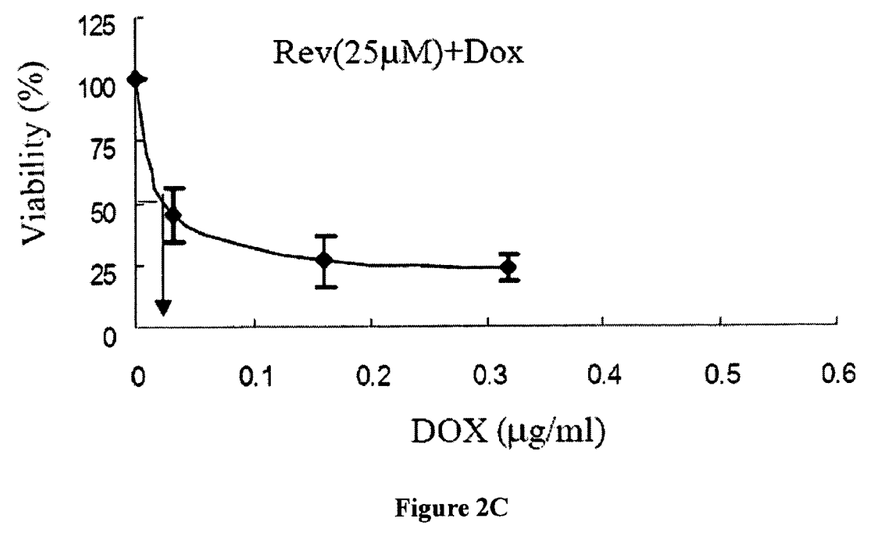
Figure 2D:
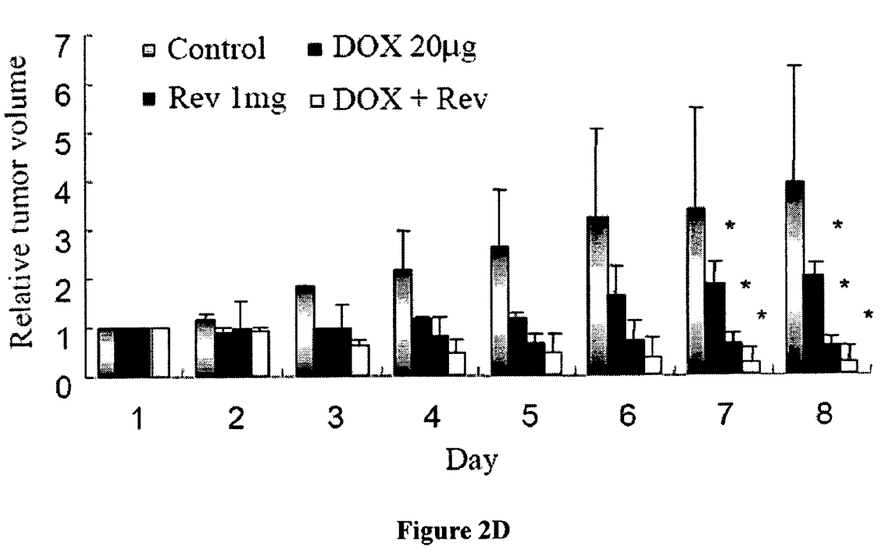
Figure 3A:
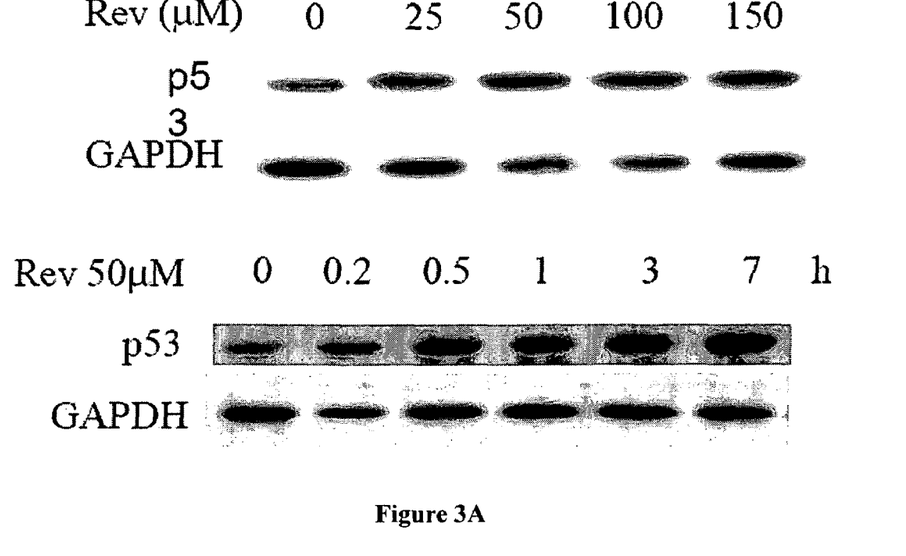
FIGS. 3A-3F are graphs illustrating Nucleophosmin/B23-binding peptide regulating the increase in protein expression of p53 according to embodiments of the present invention.
Figure 3B:
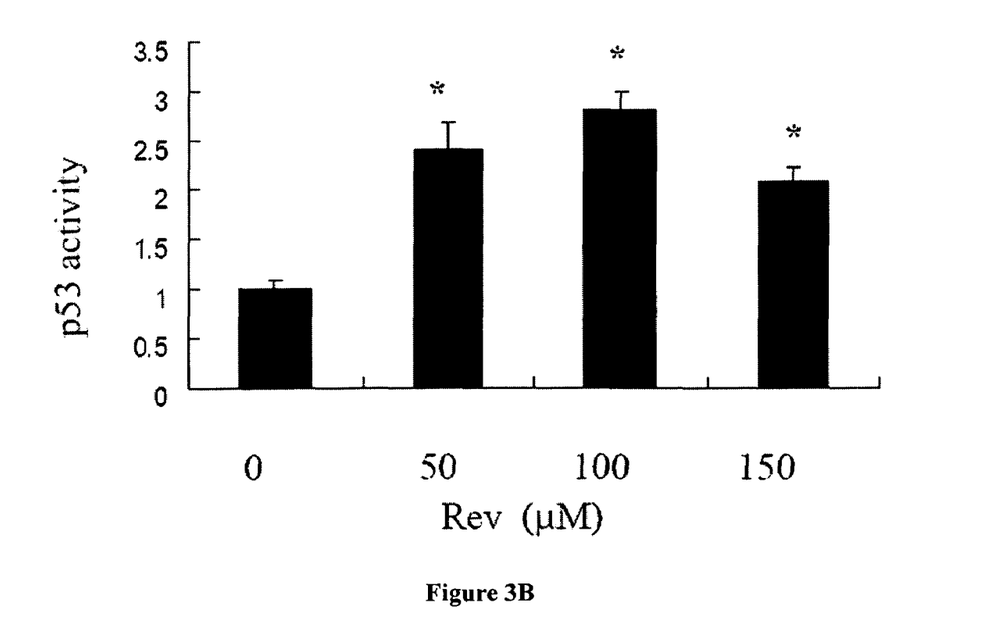

Doxorubicin (DOX), an anthracycline anti-tumor antibiotic, is active against a number of human cancers. For instance, DOX is one of the most active agents against bladder cancer. Dose-dependent decrease of viability was observed in U1 bladder cancer cells treated with DOX or with nucleophosmin/B23-binding Rev peptide (FIGS. 2A and 2B). The concentrations of DOX and Rev peptide required to produce a 50% decrease in cell viability were 0.08 µg/ml and 66.7 µM respectively. Moreover, it is interesting to note that a low dose (25 µM) of Rev peptide could potentiate the DOX-induced decrease of cell viability (FIG. 2C). Less DOX (0.03 µg/ml) was needed to induce 50% decrease of viability of U1 cells in the presence of 25 µM Rev peptide. Furthermore, we also examined the growth of tumor when DOX (20 µg/20 g body weight), Rev peptide (1 mg/20 g body weight) or DOX (10 µg/20 g body weight)+Rev peptide (0.5 mg/20 g body weight) were administered subcutaneously adjacent to the tumors in nude mice daily for 5 days. The tumor grew more slowly in mice treated with DOX than the one in the control mice treated with PBS ($p<0.05$) (FIG. 2D). The tumor in mice treated with Rev peptide did not grow but decreased in 8 days to about 30% of the initial tumor size. Significant decrease of the tumor size was also observed in mice treated with the combination of DOX and Rev peptide (FIG. 2D).

p53 protein is known to suppress tumor formation in vivo at least in part through its ability to induce cell death. The susceptibility of tumor cells to induction of cell death by cytotoxic drugs is modulated by p53 in many cases. It is then important for us to test whether the anti-tumor activity of nucleophosmin/B23-binding peptide is mediated through a p53 dependent regulation. U1 cells were therefore treated with various concentrations of Rev peptide (25-150 µM) for 3 hours or with 50 µM for various times (0.2-7 hours) (FIG. 3A). The expression levels of p53 were measured by western blotting. Treatment with Rev peptide induced a marked increase in intracellular amount of p53 (FIG. 3A). In parallel, we transfected cells with a plasmid containing the luciferase reporter gene under the control of an artificial p53 target promoter (pGL13). Measurement of p53-dependent transcription from the pGL13 promoter clearly showed an increase (2-3 fold) in the promoter activity after treatment with Rev peptide (50-150 µM) for 3 hours (FIG. 3B). No such increases of p53 protein expression and transcriptional activity were observed in cells treated with control np-NLS peptides (data not shown). Moreover, we analyzed whether the level of p53 changes upon siRNA mediated reduction of the intracellular amount of nucleophosmin/B23. Consistent with the results from the peptide treatment, p53 protein (FIG. 3C) and its dependent transcription (FIG. 3D) were also found elevated in cells treated with nucleophosmin/B23-siRNA. We then asked whether suppression of p53 gene expression by siRNA construct was able to affect the tumor growth inhibition during Rev peptide treatment. The data shown in FIG. 3E indicate that transfection with p53-siRNA abrogated the increase of p53 expression and the decrease of cell viability after Rev peptide (50 µM) treatments.

Previously, our results have implicated nucleophosmin/B23 in the regulation of PCNA promoter. To directly demonstrate that the Rev peptide is capable of blocking nucleophosmin/B23's function, a reporter assay was done. A plasmid (pD6-CAT) containing the PCNA promoter was cotransfected into NIH 3T3 fibroblasts with 0.5 µg of nucleophosmin/B23 expression plasmid (pCR3.1-FLAGB23). Cotransfection with pCR3.1-FLAGB23 led to increase in transcriptional activation. Treatment with the Rev peptide (75-100 µM) significantly inhibited such nucleophosmin/B23-mediated PCNA promoter activation (FIG. 3F).

Given that nucleophosmin/B23 could be an important molecular target for cancer suppression, the study demonstrated a novel antitumor function of the nucleophosmin/B23-binding peptides. The Rev peptide, exhibiting high binding affinity toward nucleophosmin/B23, exerts potent cytotoxicity on Ras-3T3, U1 cells and the tumors induced in nude mice. Nucleophosmin/B23 functions as an oncogene, whose over-expression fully transforms NIH-3T3 cells in a standard assay for oncogenic potential. In this regard, the example study shows that the Rev peptide could reverse the transformed phenotype of Ras-3T3 cells to normal-like phenotype. Rev peptide not only has anti-tumor effect itself but also at lower doses could potentiate the doxorubicin-induced decrease of cellular viability of the U1 bladder cancer cells as well as growth inhibition of the tumors in nude mice.

Similar to the down-regulation of nucleophosmin/B23 by anti-sense treatment, the Rev peptide, by binding and blocking the function of nucleophosmin/B23, sensitize cancer cells to growth inhibition control. Normally, the expression of cellular p53 protein is very low due to its relatively short half-life. Under stress conditions, various signaling pathways converge on the downstream mediator, p53. This results in a rapid increase in the level of p53 in the cells and activation of p53 as a transcription factor. It has been hypothesized that the cellular proteins that sense the stress communicate with p53 and ultimately regulate it. In this regard, nucleophosmin/B23 is an attractive candidate as it is rapidly up-regulated after UV irradiation as p53. Damaged DNA induces immediate response of nucleophosmin/B23. Nucleophosmin/B23 acts as a crucial regulator of p53, interacting with it, regulating its stability and transcriptional activation in the presence of different types of stress. Nucleophosmin/B23 is one important cellular protein that communicates with p53 in the acute response of mammalian cells to environmental stress.

Furthermore, a second important biological role of p53 is that it acts as a gate-keeper against the formation of cancers. Inactivation of the p53 occurs in over half of all human cancers. Down-regulation of p53 or over-expression of its mutants is associated with advanced cancers. Loss of p53 gene represents a fundamentally important step in the pathogenesis of cancer and appears to play a significant role in the treatment of cancer. Nucleophosmin/B23 over-expression at the RNA and protein levels contributes to the onset of cancer. Excess of nucleophosmin/B23 is associated with the resistance of cancer cells to induction of cell death. It has been shown that over-expression of nucleophosmin/B23 induces a cell cycle arrest in normal fibroblasts, whereas in tumor cells lacking p53 it promotes S phase. Conversely, knocking down nucleophosmin/B23 induces cell death.

Although the physiological function of nucleophosmin/B23 seems to be proapoptotic in normal fibroblasts, high level of nucleophosmin/B23 has an oncogenic potential to promote cell growth that may provoke a p53 response. Presently, we have shown that treatment with a peptide that binds and functionally blocks nucleophosmin/B23 elevates p53 transcriptional activity. Consistently, our studies have also shown that p53 increases upon siRNA mediated reduction of the intracellular amount of nucleophosmin/B23. Suppression of p53 gene expression by the p53-siRNA construct is able to abrogate the Rev peptide-induced decrease of cell viability. Taken together, these results indicate that nucleophosmin/B23-binding peptide, which could alter nucleophosmin/B23's function, exerts its anti-tumor activity and ability to induce cell death through up-regulation of p53. Nucleophosmin/B23 communicates with p53 in tumor development and in cellular response to induction of cell death.

The effect of Rev peptide on growth inhibition are also observed in many other cancer cell lines such as HeLa, HL-60, and K562.

In addition, higher doses of Rev peptide are needed to exert similar cytotoxic effect on nucleophosmin/B23 over-expressed cells. Although the effect of Rev peptide over tumor growth is clear and may be related to nucleophosmin/B23, we cannot exclude the possibility that this peptide may have another effects on tumor growth independent of p53. Since HeLa is often considered as a p53-deficient cancer cell line, Rev peptide may exert tumor growth inhibition in HeLa cells through some other transcriptional pathways independent of p53. Moreover, nucleophosmin/B23 could interact with several different factors. It is then possible that Rev peptide may interfere with interactions between nucleophosmin/B23 and those factors for growth inhibitory effect. The dissection of more possible downstream targets of nucleophosmin/B23 for cellular growth is currently being carried out. In conclusion, small molecule like a peptide that binds to the target of cancer such as nucleophosmin/B23 represent a potentially useful approach to anti-cancer biotherapeutics.

In summary a review of the Figures is given. FIGS. 1A-1D, illustrate Nucleophosmin/B23-binding peptide inhibits tumor growth of Ras-3T3 cells and tumors in nude mice. FIG. 1A shows the cytotoxic effect of different peptides (Rev, T-NLS, np-NLS). After 24 hours of exposure, cells were counted and survival was expressed as the percentage of surviving cells relative to the untreated cells. Data represent means ±standard deviations; n=3. FIG. 1B illustrates Rev peptide inhibited the anchorage-independent growth of Ras-3T3 cells. The colonies were stained and scored 12 days after seeding and the efficiencies were calculated as the percentage relative to the untreated cells. Values were expressed as the means ± standard deviations for three determinations. FIG. 1C shows that each mouse was inoculated with $3 \times 10^5$ Ras-3T3 cells (one site/mouse) on day 0. The administration (intraperitoneally) of Rev peptide (1.5 mg/20 g body weight) or T-NLS, np-NLS peptide (10 mg/20 g body weight) was started on day 2 and stopped on day 15. Mean tumor volume ±standard deviation for each treatment group was plotted (n=5). Statistical differences in tumor volumes were determined by Student's t-test. In FIG. 1D, Rev peptide (1 mg/20 g body weight) was injected into the subcutaneous tissue adjacent to the tumor when the tumor volume had reached a mean value of 90 mm$^3$. Tumor volumes of Rev- and PBS-treated (control) mice were plotted (n=5). A Student's t-test was used for statistical analysis. Results shown are representative of three independent experiments.

FIGS. 2A-2D illustrate Rev peptide potentiated doxorubicin-induced anti-tumor activity against U1 bladder cancer cells and tumors in nude Mice. U1 ($3 \times 10^5$) cells were treated with doxorubicin (DOX, 0.032-1.0 µg/ml). FIG. 2A is Rev peptide (50-200 µM), FIG. 2B is alone or concurrently treated with DOX (0.032-0.32 µg/ml) and FIG. 2C is 25 µM Rev. After 24 hr of exposure, cells were counted and survival was expressed as the percentage of surviving cells relative to the untreated cells. Data represent means ±standard deviations; n=3. In FIG. 2D, each mouse was inoculated with $3 \times 10^5$ Ras-3T3 cells (one site/mouse). Doxorubicin+Rev peptide was injected subcutaneously into the tissue adjacent to the tumor when the tumor volume had reached a mean value of 90 mm$^3$. Tumor volumes of DOX (20 µg/20 g body weight), Rev (1 mg/20 g body weight), DOX (10 µg/20 g body weight)+ Rev (0.5 mg/20 g body weight) and PBS-treated (control) mice were plotted (n=5). The relative tumor volumes were expressed as percentages of the initial volumes at first day of treatments. *p<0.05, as compared with control mice. A Student's t-test was used for statistical analysis. Results shown are representative of three independent experiments.

Figure 3C:
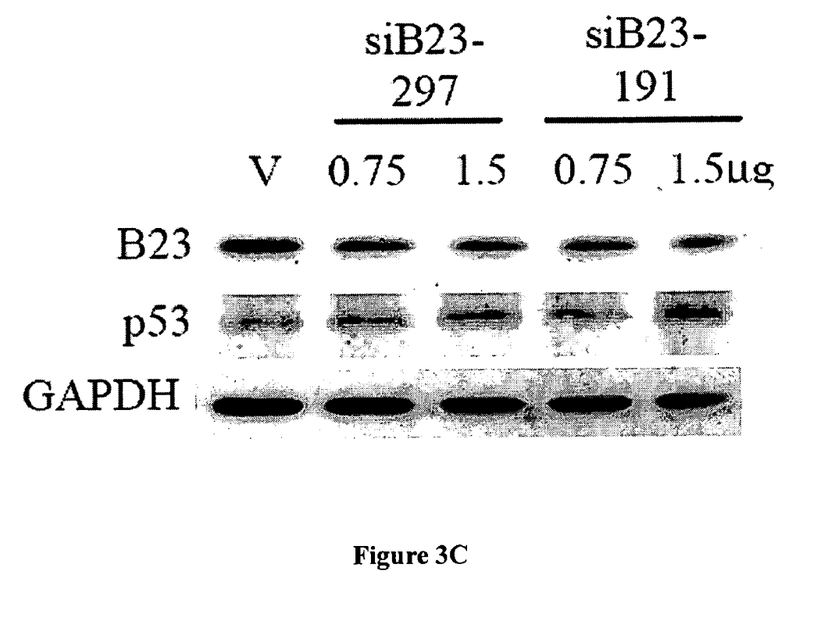
Figure 3D:
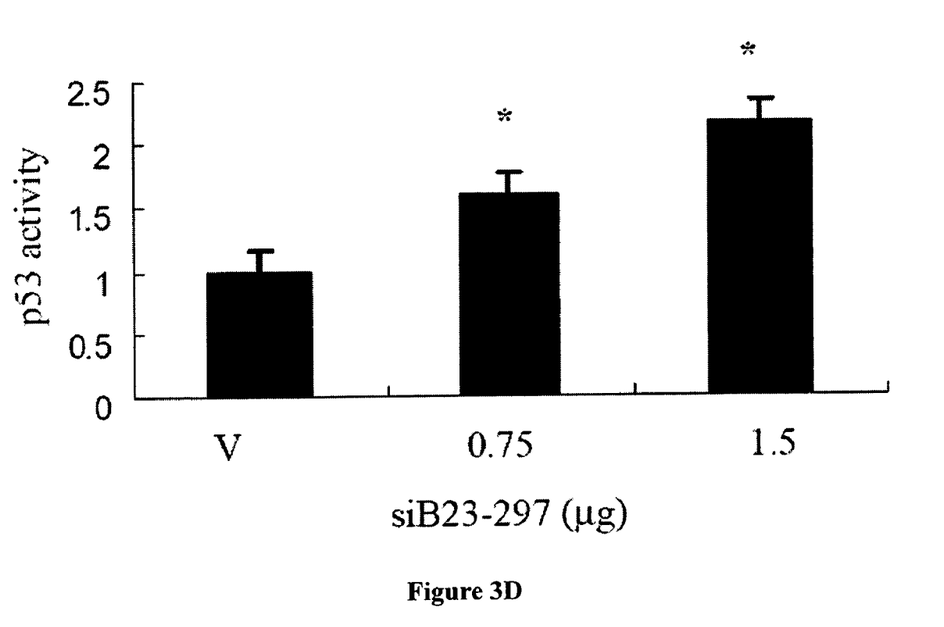
Figure 3E:
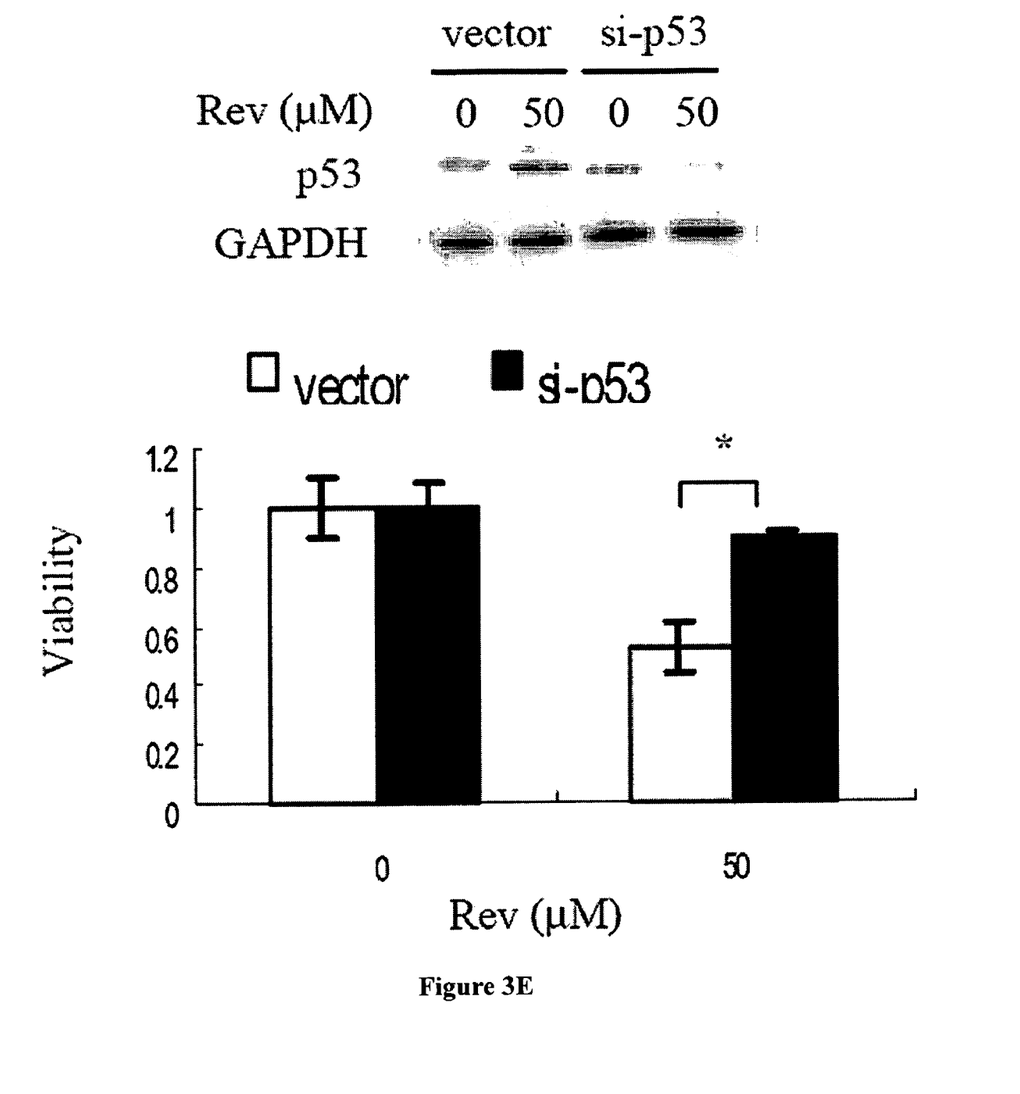
Figure 3F:
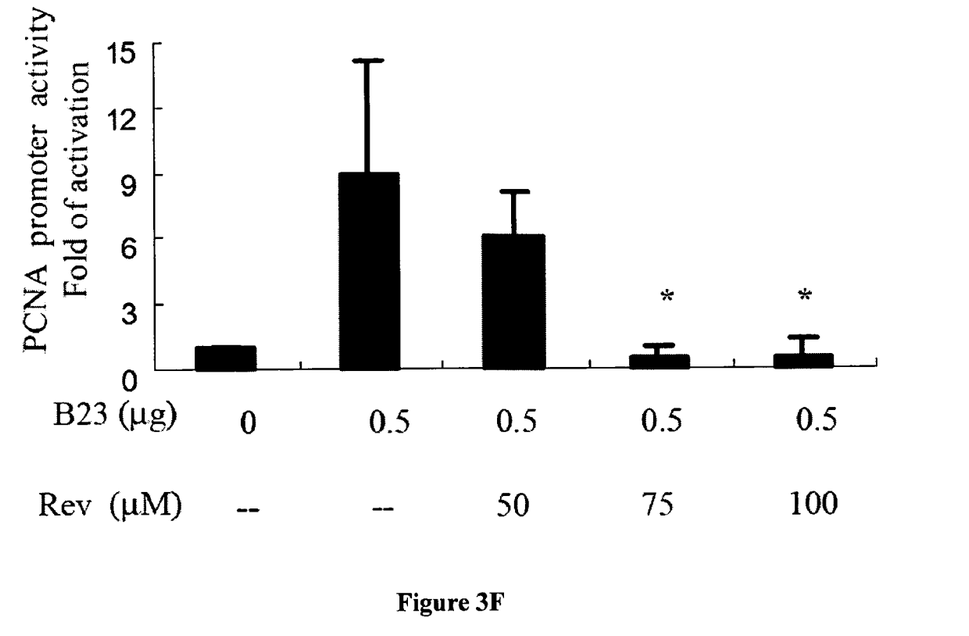

FIGS. 3A-3F illustrate Nucleophosmin/B23 regulates the increase in protein expression of p53. In FIG. 3A, U1 ($3 \times 10^5$) cells were treated with various concentrations of Rev peptide (25-150 µM) for 3 hours or with 50 µM for various times (0.2-7 hours). Total cell lysates were analyzed by western immunoblotting using antibodies specific for p53 and GAPDH. In FIG. 3B, p53-dependent luciferase activity of the reporter plasmid pGL13 in U1 cells. U1 cells were treated with various concentrations of Rev peptide (50-150 µM) for 3 hours before the luciferase assay. Data are representative of three independent experiments and are normalized by co-transfection of a CMV-β Gal expression vector. *p<0.05, as compared with control untreated cells. In FIG. 3C, U1 cells were treated with nucleophosmin/B23-siRNA (siB23-297, siB23-191) or vector (V) for 24 hours. Total cell lysates were analyzed by Western immunoblotting using antibodies specific for nucleophosmin/B23, p53 and GAPDH. In FIG. 3D, p53-dependent luciferase activity of the reporter plasmid pGL13 in nucleophosmin/B23 siRNA treated U1 cells. U1 cells were treated with nucleophosmin/B23-siRNA (siB23-297) or vector (V) for 24 hours before the luciferase assay. Data are representative of three independent experiments and are normalized by co-transfection of a CMV-β Gal expression vector. *p<0.05, as compared with vector-treated cells. In FIG. 3E, U1 p53-siRNA-transfected (si-p53) or vector-transfected (V) cells were treated with Rev peptide (50 µM). After 3 hours, cells were harvested and were analyzed by Western immunoblotting using antibodies specific for p53 and GAPDH. In parallel, cells were also counted and cell viability was determined after 12 hours of Rev peptide treatment. Data represent means ± standard deviations; n=3. *p<0.05, as compared with vector-treated cells. In FIG. 3F, Rev peptide blocks the nucleophosmin/B23-induced PCNA promoter activity in NIH 3T3 fibroblasts. NIH-3T3 cells were transfected with 2.0 µg of pD6-CAT (PCNA promoter reporter), 0.1 µg of pCR3.1-Luc (as a control for transfection efficiency), 0.5 µg nucleophosmin/B23 cDNA plasmid, pCR3.1-FLAGB23, and pGEX. Two hours after transfection, cells were treated with various doses of Rev peptide (50-100 µM). After 44 hours of Rev peptide treatment, cells were harvested. The cell extracts containing equal amounts of proteins were analyzed for CAT activity and luciferase activities. CAT units were normalized to luciferase values to control for transfection efficiency. Fold activation was determined by dividing the CAT activity of each sample by the basal CAT activity in the absence of pCR3.1-FLAGB23. Bars, means of triplicates ±standard deviations. *p<0.05, as compared with Rev peptide untreated cells.

It will be apparent to those skilled in the art that various modifications and variations can be made to the present invention without departing from the scope or spirit of the invention. In view of the foregoing, it is intended that the present invention cover modifications and variations of this invention provided they fall within the scope of the invention and its equivalent.

---

What is claimed is:

1. A method of inhibiting cell growth comprising the step of:
blocking the function of Nucleophosmin/B23 within a cell comprising administering a Nucleophosmin/B23 binding peptide wherein said binding peptide is Rev-NLS and said blocking includes the step of up-regulating the transcriptional activity of p53.

2. The method of claim 1 wherein the cell is a tumor cell or cancer cell.

3. The method of claim 1 wherein said Nucleophosmin/B23-binding peptide is injected into a patient having the a tumor cell or cancer cell.

4. The method of claim 1 wherein the peptide is synthesized.

5. The method of claim 3 wherein the peptide dose is determined in relation to a body weight of a patient.

6. The method of claim 1 wherein the peptide is used in conjunction with an anti-tumor antibiotic.

7. The method of claim 6 wherein the anti-tumor antibiotic is Doxorubicin.

8. A method of inhibiting tumor growth in a patient comprising:
   injecting Nucleophosmin/B23-binding peptide Rev-NLS into the patient; and
   repeating injecting daily until tumor growth stabilizes or the tumor size decreases.

9. The method of claim 8 wherein the peptide is synthesized.

10. The method of claim 8 wherein the peptide dose is determined in relation to a body weight of the patient.

11. The method of claim 8 wherein the peptide is used in conjunction with an anti-tumor antibiotic.

12. The method of claim 11 wherein the anti-tumor antibiotic is Doxorubicin.

13. A method of inhibiting cell growth in a patient comprising the step of:
   administering Rev-NLS to molecular targets associated with the regulation of growth control pathways, cellular differentiation, and apoptosis.

14. The method of claim 13 wherein the peptide is injected into the patient.

15. The method of claim 13 wherein the cell is a tumor cell or cancer cell.

* * * * *

SEQUENCE LISTING

<160> NUMBER OF SEQ ID NOS: 5

<210> SEQ ID NO 1
<211> LENGTH: 13
<212> TYPE: PRT
<213> ORGANISM: Homo sapiens

<400> SEQUENCE: 1

Ala Arg Arg Asn Arg Arg Arg Arg Trp Arg Glu Tyr Cys
 1               5                   10

<210> SEQ ID NO 2
<211> LENGTH: 12
<212> TYPE: Prt
<213> ORGANISM: Homo sapiens

<400> SEQUENCE: 2

Pro Lys Lys Lys Arg Lys Val Glu Asp Pro Tyr Cys
 1               5                   10

<210> SEQ ID NO 3
<211> LENGTH: 18
<212> TYPE: PRT
<213> ORGANISM: Homo sapiens

<400> SEQUENCE: 3

Lys Arg Pro Ala Ala Thr Lys Lys Ala Gly Gln Ala Lys Lys Lys Lys
 1               5                   10                  15

Tyr Cys

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
caccaccagt ggtcttaag cttaagacca ctggtggtg                          38

<210> SEQ ID NO 5
<211> LENGTH: 38
<212> TYPE: DNA
<213> ORGANISM: Artificial Sequence
<220> FEATURE:
<223> OTHER INFORMATION: Primer

<400> SEQUENCE: 5
gcagaggcaa tgaattacg cgtaattcat tgcctctgc                          38